United States Patent [19]

Leong et al.

[11] Patent Number: 5,686,091
[45] Date of Patent: Nov. 11, 1997

[54] BIODEGRADABLE FOAMS FOR CELL TRANSPLANTATION

[75] Inventors: Kam W. Leong, Ellicot City; Hungnan Lo; Sudhakar Kadiyala, both of Baltimore, all of Md.

[73] Assignee: The Johns Hopkins University School of Medicine, Baltimore, Md.

[21] Appl. No.: 219,017

[22] Filed: Mar. 28, 1994

[51] Int. Cl.$^6$ ............................................. A61F 2/00
[52] U.S. Cl. .................. 424/426; 264/45.6; 264/45.8; 264/45.9; 264/46.4; 264/46.6; 264/46.8; 264/48; 264/53; 264/41; 435/246; 428/306.6; 428/308.4; 428/315.5; 623/16
[58] Field of Search .................... 264/45.6, 45.8, 264/45.9, 46.4, 46.6, 46.8, 48, 53, 41; 435/246; 424/426; 428/306.6, 308.4, 315.5; 623/16

[56] References Cited

U.S. PATENT DOCUMENTS

| | | | |
|---|---|---|---|
| 3,812,224 | 5/1974 | Smith et al. | 264/28 |
| 4,186,448 | 2/1980 | Brekke | 3/1.9 |
| 4,826,945 | 5/1989 | Cohn et al. | 528/76 |
| 5,035,713 | 7/1991 | Friis | 623/16 |
| 5,102,983 | 4/1992 | Kennedy | 528/354 |
| 5,256,765 | 10/1993 | Leong | 528/398 |

OTHER PUBLICATIONS

Success of prosthetic devices fixed by ingrowth or surface interaction P. Ducheyne, *Acta Orthopaedica Belgica*, pp. 144–166, 1985.

Learning How To Suppress Cancer Jean Marx, *Science*, 261:1385–1387, Sep. 10, 1993.

Tissue Engineering by Cell Transplantation Using Degradable Polymer Substrates Cima, et al., *Journal of Biomechanical Engineering*, 113:143–151, May 1991.

Preparation of poly(glycolic acid) bonded fiber structures for cell attachment and transplantation Mikos, et al., *Journal of Biomedical Materials Research*, 27:183–189, 1993.

*Primary Examiner*—Frederick Krass
*Attorney, Agent, or Firm*—Leydig, Voit & Mayer

[57] ABSTRACT

A structurally rigid biodegradable foam scaffold useful for cell transplantation is provided. The foam can be loaded with nutrients and/or drugs that elute from the foam during transplant to promote growth of the cells. The foam, which features a continuous network of pores, is fabricated using a novel method involving phase separation and consequent expansion upon sublimation of a liquid solvent, preferably naphthalene.

24 Claims, 4 Drawing Sheets

5,686,091

BIODEGRADABLE FOAMS FOR CELL TRANSPLANTATION

BACKGROUND OF THE INVENTION

1. Field of the Invention

This invention relates to tissue engineering by cell transplantation using degradable polymer substrates. More particularly, the invention relates to a method for preparing a biodegradable foam useful as a substrate for cell transplantation and drug delivery.

2. Description of Related Art

Several approaches to cell transplantation have been explored in the past. Reconstruction of defective tissue by means of an autograft or an allograft provides the best results. However, limited availability of tissue for grafting and the potential for transmission of diseases like AIDS and hepatitis make the use of autografts and allografts less attractive. Consequently, various alternative means have been devised for accomplishing cell transplantation.

The feasibility of cell survival at ectopic sites was initially demonstrated by injecting suspensions of dissociated cells into other tissues such as fat, liver or spleen, with the stroma of the host tissue providing the only matrix for cell attachment and reorganization. Liver cells transplanted in this fashion have been shown to persist, with normal hepatocellular architecture as observed histologically, for periods up to 15 months. Functional integrity of the transplanted cells has been demonstrated directly by assays of liver enzyme activity, immunostaining, and mRNA analysis for liver specific gene products. However, a sustained increase in cell mass above that injected has not been observed, thus underscoring the limitations of trying to achieve growth and structuring of new tissue in the context of mature tissue without creating a template to guide new tissue growth (L. G. Cima, et al., *J. Biomech. Engr.*, 113:143–151, 1991).

Alternatively, biodegradable polymers have been used to regenerate metabolic organs, such as the liver and pancreas, and repair structural tissues like cartilage and bone by cell transplantation. To create organ function, donor material is obtained, the tissue is dissociated into individual cells, the cells are attached to a polymer cell growth scaffold, and the device is implanted to a place where the attached cells grow and function.

There have been attempts to culture cells on polymeric foams. Most of the polymeric foams used for tissue engineering applications are made from poly(lactides (PLA), poly(glycolides) (PGA), or a combination of the two (PLGA). For instance, Mikos, et al. (*Biodegradable Cell Transplantation Devices for Tissue Regeneration*, Materials Research Society Symposium Proceedings, 252:352–358, 1992) used solvent casting of a PLGA-NaCl mixture followed by particulate leaching to fabricate a foam. However, the maximum level of porosity in this process is limited due to the difficulty of suspending salt particulates in the polymer solution. Furthermore, the crystalline structure of the sodium chloride salts gives sharp edges to the pores of the resulting foam, which are not conducive to cell growth. Some of these problems can be overcome by making thin films of the foam and laminating them. Nevertheless, complex shaped implants cannot be easily compacted and the process is rather time-consuming.

Alternatively, a tassel of braided fibers 14 µm in diameter constructed of poly(lactic-co-glycolic acid) and fiber-based felts have been used to fabricate porous devices useful in transplant of hepatocytes to regenerate liver function and of chondrocytes to regenerate cartilage function (C. A. Vacanti, et al., *Plast. Reconstr. Surg.*, 88:753–759, 1991; L. G. Cima, et al., *J. Biomech. Eng.*, 113,143–151, 1991). Chrondrocytes cultured in vitro on polyglycolic acid) (PGA) fiber meshes yielded a 8.3-fold increase in cell density after six weeks, equaling the performance reported for normal bovine articular cartilage. However, the pore size and distribution are very difficult to control in these devices.

Moreover, to be useful for cell attachment and transplantation, tissue scaffolding must provide a firm substrate to the transplanted cells and often must be configured into shapes similar to those of the tissue to be repaired. Tassels and felts lack the necessary structural stability for in vivo repair.

Another process utilizing two sheets of non-woven PGA and PGA fabrics with fiber diameter of 5 µm were overlapped and sewn together by K. Ito, et al. (*Materials Res. Soc. Symp. Proc.*, 252:359–365, 1992) to provide scaffolding for cells to grow on. The PGA mesh was immersed in methylene chloride containing PLA or PLGA to coat the fibers and thereby provide some structural support. The structural rigidity of the scaffold produced in this manner is limited. The structural rigidity of the scaffold was further improved by Mikos, et al. (*J. Biomed. Matl. Res.*, 27:183–189, 1993) by using a "fiber bonding" technique for preparing structural interconnecting fiber networks and different shapes for organ implants. Utilizing this process non-woven fibers are bonded together by immersing a nonbonded fiber structure of polymer A into a solution of polymer B. A solvent is employed which is not a solvent for Polymer A. The solvent is allowed to evaporate, the composite consisting of fibers of Polymer A embedded in a matrix of polymer B is heated above the melting temperature of polymer A to weld the fibers at their cross-points, and then polymer B is selectively dissolved. The resultant bonded fiber structure of Polymer A has considerable rigidity, but the porosity and pore distribution is limited by that of the fiber mesh used in the fabrication.

Thus, the need exists in the art for more and better foam polymer scaffolds for supporting the maturation and proliferation of implanted cells. In addition the need exists for a foam scaffold having pores of sufficient number, size and interconnectedness to be suitable for loading therein drugs or nutrients useful in promoting the growth of implanted cells. Due either to the high temperatures of fabrication used or the need to leach out the porogens, none of the procedures known in the art is suitable for yielding a foam scaffold loaded with drugs and/or nutrients. These drawbacks severely limit the appeal of porous scaffolds produced by the prior art methods for growth of implanted cells. The capacity of a cell scaffold for loading drugs and/or nutrients for controlled delivery to the developing tissue is a highly desirable feature that contributes to the successful development and proliferation of implanted cells.

SUMMARY OF THE INVENTION

A structurally rigid, highly porous foam graft suitable for culture of transplanted cells seeded therein is produced by dissolving a biocompatible polymer in an organic liquid solvent having a melting point in the range from about 30° C. to about 90° C., quenching the solution, and sublimating the solvent. Addition of additives, such as cell growth nutrients and/or drugs, to the polymer solution results in a foam graft from which the additives elute into the growth environment of the cells. The preferred polymers are polylactic acid and polyphosphoesters, and the preferred solvent is naphthalene for its low melting temperature and ease of removal by sublimation.

A DETAILED DESCRIPTION OF THE INVENTION

Figure 1:
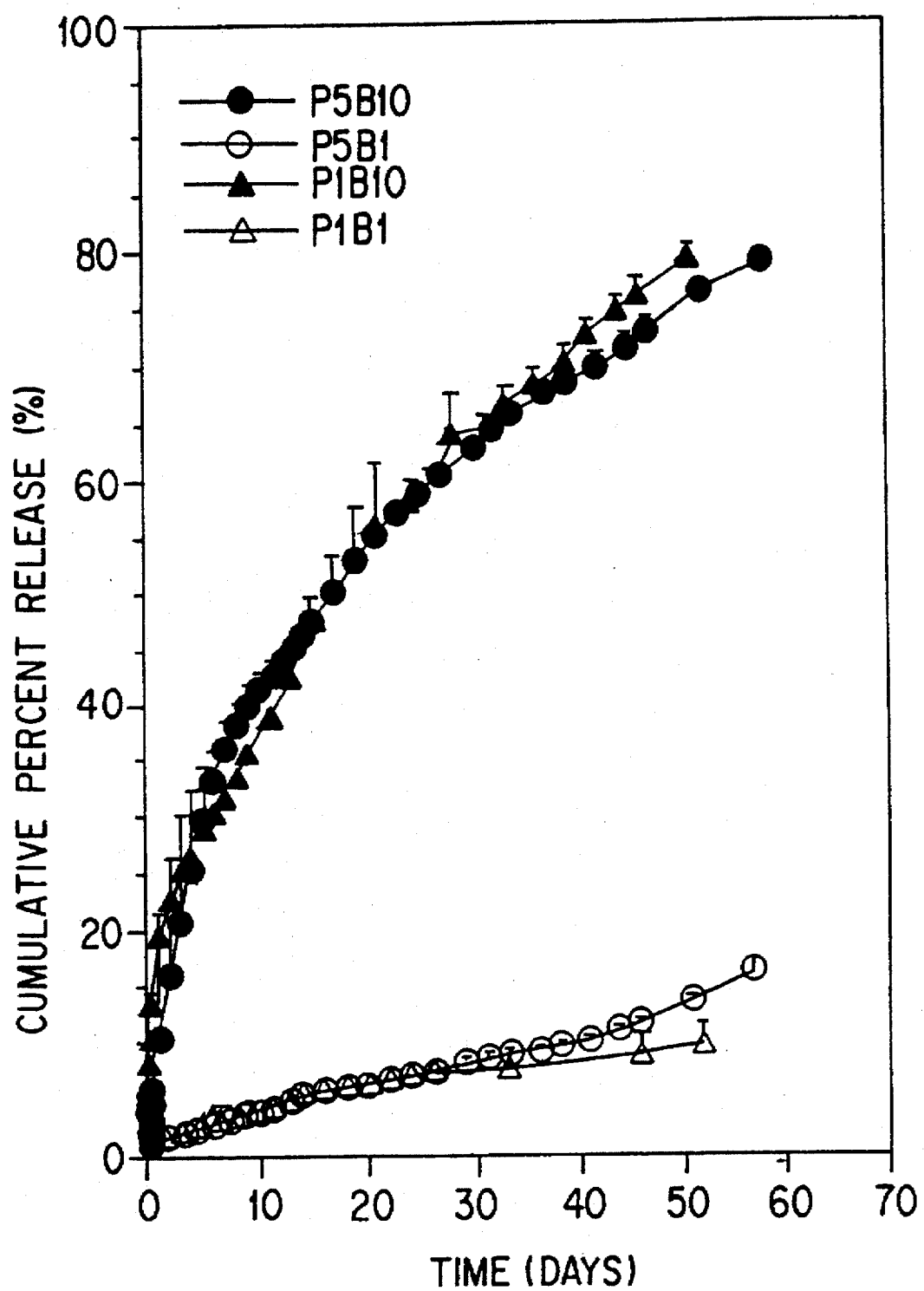
FIG. 1 is a graph showing in vitro release of bromothymol blue (BTB) from four PLLA foams in 0.1M phosphate buffer (pH 7.4) at 37° C. Samples of foams made from polymer solutions containing 1 and 5 wt % of PLLA were each loaded with an additional 1 or 10 wt % of BTB. P5B10=10 wt % BTB loaded on foam made of 5% PLLA solution; P5B1=1 wt % BTB loaded on foam made of 5% PLLA solution; P1B10=10 wt % BTB loaded on foam made of 1% PLLA solution; and P1B1=1 wt % BTB loaded on foam made of 1% PLLA solution.

This invention provides a new process to fabricate highly porous biodegradable foams with various pore morphologies and shapes. The three-dimensional foams are designed to mimic the natural connective tissues of the body. High porosity is required to accommodate a large number of cells and to allow for efficient transport of nutrients and waste products. Also, the vascularization and nature of tissue ingrowth depend on the pore diameter and interconnecting structure.

Highly porous foams are two-phase systems consisting of a continuous polymer phase and a continuous gaseous phase. The foam fabrication process described herein works on the principle of phase separation in a polymer solution (J. W. Cahn and J. E. Hilliard, *J. Chem. Phys.*, 28:258, 1958). The foam morphology and pore distribution depend on the mechanisms of the phase separation. Phase separation in homogeneous solutions will, in principle, proceed either by metastable nucleation or by spinodal decomposition. Which of these mechanisms will be followed depends on quenching temperature, solution concentration, and the rate of cooling. The initial structures connected with these mechanisms can be characterized as follows: in the first case, nuclei will be formed and grow until equilibrium is reached; in the second case interconnected structures can be formed (T. Nishi, et al., *Macromolecules*, 8:227, 1975). In both cases these primary structures can be destroyed by coalescence of the segregated regions, resulting in a more random structure (E. D. Siggia, *Phys. Rev.*, A20:595, 1979; H. Tanaka, et al., *Phys. Rev. Lett.*, 59:692, 1987).

For optimum cell growth within the pores of the foam, a substantially uniform pore distribution is required. Therefore, during the foam fabricating process of this invention, all conditions are selected to ensure the phase separation is limited to the early stages of spinodal decomposition. Most particularly, the polymer solution is held in the region of the phase separation for the shortest time possible. The shorter the time that the polymer solution is held in the region of the phase separation, the more fibrous the foam will be as implied by the coalescence theory. Preferably, therefore, the polymer solution is quenched in liquid nitrogen to arrest the phase separation at the early stages of spinodal decomposition and the solvent is subsequently removed by sublimation, leaving behind a substantially evenly distributed pore network.

Selection of the solvent is critical to the practice of this invention. The following characteristics of the solvent must be considered in making its selection: (1) the solvent should be easy to remove by a process of simple sublimation at a temperature at which the polymer/solvent solid mixture remains immobilized, thereby preserving the foam morphology; (2) the melting point of the solvent pressure must be low enough to minimize degradation of incorporated bioactive agents; (3) the progress of phase separation should be ceased by quenching the whole solution to a temperature below the melting point of the solvent. Generally, therefore, the solvent is an organic compound with a melting point in the range between 30 and 90 degrees Centigrade. Examples of solvents suitable for use in the practice of this invention are phenol, 1,4 dichlorobenzene, trichlorobenzene and naphthalene. The preferred solvent for the practice of this invention is naphthalene, which meets all of the above criteria.

Polymers used as templates for cell transplantation must be biocompatible and biodegradable in addition to acting as adhesive substrates for cells, promoting cell growth, and allowing retention of differentiated cell function. Such materials must also possess physical characteristics allowing for large surface to volume ratios, mechanical strength and easy processing into complex shapes, such as for bone substitutes. The resulting polymeric device should also be rigid enough to maintain the desired shape under in vivo conditions.

The three-dimensional polymer foam provides a sturdy scaffold for the transplanted cells and a means of organization to the ingrowing tissue. In addition, the high degree of porosity allow the accommodation of a large number of cells and ensures a high rate of cell growth. Also, for tissue ingrowth, vascularization, and diffusion of nutrients, pore diameter much larger than the implanted cell diameter is required as well as a structure of interconnection between pores to form a pore network (P. Ducheyne, *Acta Orthopaedica Belgica*, 51:144–161, 1985).

The polymers useful in the practice of this invention are substantially biodegradable, non-toxic, and physiologically compatible. The biodegradable polymer must be selected for biocompatibility at the time of implant, and the products of its degradation process must also be biocompatible. Additional parameters that play an important role include the mechanical properties of the material and, for most applications, the match between the biodegradation kinetics of the polymer and the rapidity of the healing process. Few polymers meet these requirements; however, polyglycolic acid, polylactic acid and copolymers of the two are generally used as biodegradable materials. These α-hydroxy-carboxylic acids have slow degradation kinetics and relative stiffness. In addition, polyglycolic and polylactic acid copolymerized with glycolide or lactide monomers produce a polymer possessing the requisite properties. Other copolymers used as bioabsorbable materials are polyethylene oxide/polyethylene terephthalate copolymers (Reed, et al., *Trans. Am. Soc. Artif. Intern. Organs*, 1977, page 109). In addition, U.S. Pat. No. 4,826,945 discloses copolymers of lactic or glycolic acid or combinations of the two with hydroxy-ended flexible chains, preferably poly(alkylene glycols) of various molecular weights, to produce absorbable polymers possessing increased flexibility and covering a wide range of biodegradation rates.

Thus, polymers suitable for use in the practice of this invention include poly(lactic acid) (PLLA), poly(glycolic acid) (PGA), poly(lactide-co-glycolide) (PLGA), bisphenol-A based poly(phosphoester)s such as poly(bisphenol A-phenylphosphonate) (BPA/PP, poly(bisphenol A-ethylphosphate) (BPA/EOP), poly(bisphenol A-ethylphosphonate) (BPA/EP), poly(bisphenol A-phenylphosphonate) (BPA/POP), poly[bis(2-ethoxy) hydrophosphonic terephthalate] (PPET), and copolymers of the BPA series and PPET. The preferred polymers for the practice of this invention are polymers of polylactic acid (PLLA) and polyphosphoester (BPA/PP), which when used in the process of this invention afford good control of the porosity, pore size, and microstructure of the biodegradable foams for cell transplantation.

Cells seeded onto the foams for growth generally range from about 7–15 μm in diameter. Although one skilled in the art will appreciate that any number of different cell types could be used in the paractice of the method of this invention, the preferred cell types are osteoblasts, condrocytes, hepatocytes, and fibroblasts.

The concentration of polymer in the solvent should be selected to yield pore diameters larger than 20 μm, for instance 20 to 100 μm. The preferred pore diameter is in the range from about 20 to 500 μm, or 50 to 100 μm to be readily accessible for cell ingrowth.

In the method for making the biodegradable foams for cell transplant, the polymer is first dissolved into the molten solvent. The polymer solution is then transferred to an atomizer kept heated above the melting point of the solvent at all times. The polymer solution is atomized by the atomizer and sprayed onto a cold surface causing solidification of the spray layer by layer. The shape of the solidified spray will be similar to the shape of the mold it is sprayed into. The solid block is then exposed to temperature and pressure selected to cause sublimation of the solvent. For naphthalene, the preferred solvent of this invention, the block of solidified spray is exposed to a 10 millitorr atmosphere at 40° C. for twelve hours to remove the naphthalene.

An alternative procedure is to solvent cast the polymer solution into a heated mold, followed by quenching, for example, in liquid nitrogen. Both methods result in structurally rigid foams. However, the atomized particles have a large surface area to volume ratio. Consequently, heat transfer is very rapid and the quenching is more efficient when the polymer solution is atomized. Due to the nature of atomizing, materials deposited during the fabrication are loosely packed, resulting in formation of macropores as well as micropores in the foams. The formed macroporous structure could greatly facilitate cell seeding and nutrient transport. The micropores are consistent in both the casting and atomizing process.

The porosity, pore size, and pore morphology can be controlled by varying the concentration of polymer in the solution, the quenching rate and sublimation conditions, and the type of polymer selected. For instance, a foam containing 1 wt % of PLLA formulated in naphthalene results in a foam having an average pore size of about 100 μm in diameter, while a foam containing 5 wt % of PLLA in naphthalene had a pore size of approximately 50 μm in diameter. By contrast, foam made from 5 wt % BPA/PP exhibits a different morphology consisting of beads connected together. As a general rule a polymer solution containing a higher concentration of polymer results in a smaller average pore diameter in the foam. In general, faster quenching rates result in smaller pores. However, the effect depends on solution systems.

Figure 3:
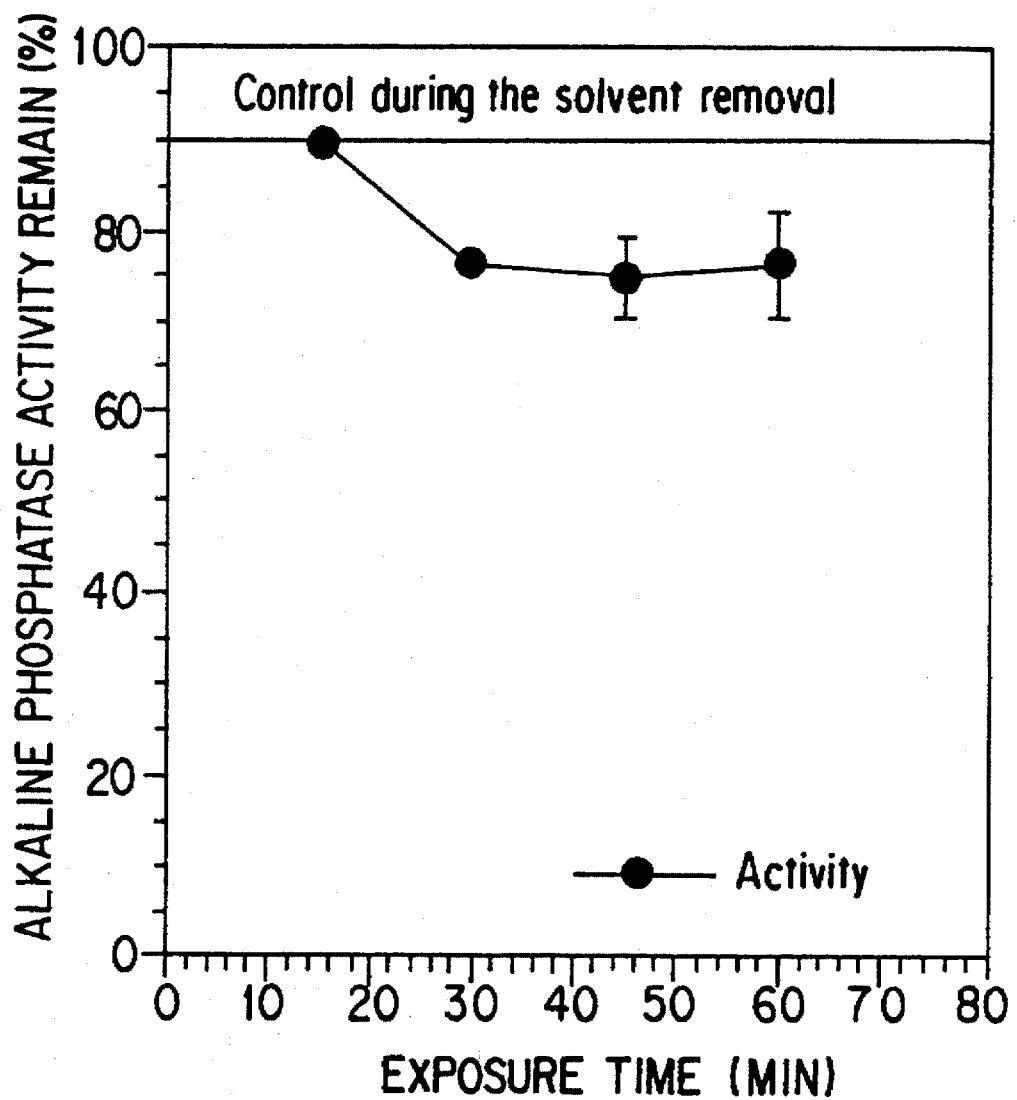
FIG. 3 is a graph showing loss of alkaline phosphatase activity with time during foam fabrication.

A particular feature of the present invention is the preparation of a foam that incorporates additives for subsequent release in a controlled fashion, i.e., as the implanted biodegradable foam dissolves due to contact with the bodily tissues and fluids. Addition of various nutrients or drugs into the polymer solution results in incorporation of the additives into the polymer foam, from which they are released during implant. However, only additives that can withstand the melting temperature of the solvent without substantial loss of activity are suitable for loading into the foams. Enzymes have been shown to survive at high temperatures in a nonaqueous environment (A. Zaks, et al., *Science*, 224:1249, 1984; *J. Biol. Chem.*, 263(7):3194, 1988). For example, FIG. 3 shows that alkaline phosphatase retained more than 70% activity after exposure to the sublimation temperature of naphthalene (80° C.) for one hour (See also Example 6 below).

Any nutrient that retains at least 50% of its activity after exposure to the melting temperature of the solvent for about 1 hour is considered suitable for loading into the foams of this invention. A nutrient is any substance that contributes to the growth and maintenance of the cells seeded into the foam scaffold. For example, osteoinductive substances, such as bone morphogenetic proteins (BMP), epidermal growth factor (EGF), fibroblast growth factor (FGF), platelet-derived growth factor (PDGF), insulin-like growth factor (IGF-I and -II), TGF-β, and dexamethason, can be loaded into a foam bone scaffold or mold to encourage bone growth in the process of bone reconstitution.

The partition of the nutrient between the polymer and the culture medium (mostly composed of water) used determines the leach rate of the nutrient during implantation. For instance, when the additive loaded into the foam is only 1% (1 mg/ml) of aqueous solubility, a higher additive release rate results from loading the foam with 10 wt % of the additive than from loading the foam with 1 wt % of the additive, independently of whether the polymer solution contains 1 or 5 wt % of the polymer. However, when the solubility of the nutrient in water is 20 times higher, release is faster from a 1 wt % polymer foam than from a 5 wt % foam.

The following examples illustrate the manner in which the invention can be practiced. It is understood, however, that the examples are for the purpose of illustration and the invention is not to be regarded as limited to any of the specific materials or conditions therein.

EXAMPLE 1

Formation of Foam

Two polymer solutions were made by dissolving the polymer in molten naphthalene around 85°–90° C. (99% purity, Aldrich Chemical Co., Milwaukee, Wis.). The first solution utilized polylactic acid (PLLA) (Zimmer, Warsaw, Ind.) with molecular weight ($M_w$) of 500,000. For use in the second solution poly(BPA/PP) was synthesized by interfacial polycondensation as previously described (M. Richards et al., *J. Polym. Sci., A: Polym. Chem.*, 29:1157, 1991). Molecular weight of the BPA/PP polymer was determined by gel permeation chromatograph (GPC) as 50,000 Dalton.

The polymer solution was cast into a heated mold by quenching into liquid nitrogen. The solid block was then exposed to a 10 millitorr atmosphere at 50° C. for 12 hours to remove the naphthalene. The porosity was controlled by varying the concentration of the polymer solutions.

EXAMPLE 2

Characterization Using Scanning Electron Microscopy (SEM)

SEM samples were coated with gold using the Hummer C sputter-coater (Anatech Ltd., Alexandria, Va.). The gas pressure was set at 40–80 millitorr and the current was 10 mA for a coating time of 100 seconds. An Amray (Series 1810) scanning electron microscope operating at 20 kV was used for examination. Foams were made from solutions containing 1 and 5 wt % of PLLA in molten naphthalene and from a solution containing 5 wt % BPA/PP were examined.

EXAMPLE 3

Determination of Porosity

The pore volume and surface area of the foams were determined by mercury porosimetry (Model 30K-A-1, Porous Materials, Inc., Ithaca, N.Y.). Polymer densities as measured by bulk density analyzer were 0.049 g/cm$^3$ for foams made from 1 wt % PLLA and 0.098 g/cm$^3$ for foam made from 5 wt % PLLA. The filling pressure of the mercury during the porosimetry analysis was recorded up to 10 psi. This pressure corresponds to the energy required to intrude mercury into pores of 20 µm. Therefore, the pore volume, pore surface area, and porosity reported here are the values of pores with diameters larger than 20 µm. As cells seeded onto the foams generally range from about 7–15 µm in diameter, the reported values represent pores accessible for cell ingrowth. The physical properties of the PLLA foams are shown in Table 1 below.

TABLE 1

| Solution Concentration (wt % PLLA solution) | 1 | 5 |
| --- | --- | --- |
| Pore Surface Area (m$^2$/g) | 1.2952 | 0.7919 |
| Pore Volume (cm$^3$/g) | 17.7474 | 7.1980 |
| Porosity (%) | 87 | 71 |
| Density (g/cm$^3$) | 0.049 | 0.098 |

EXAMPLE 4

Formation of Model Bone

To illustrate the fabrication of a complex shaped implant using the phase separation method of this invention, a model of a rabbit tibia was fabricated. The method of Example 1 was used with a polymer solution concentration of 5 wt % PLLA. The polymer solution was cast into a mold in the shape of the rabbit tibia heated to 80° C. and then quenched into liquid nitrogen.

EXAMPLE 5

Controlled Release Capability of Foams

A unique advantage of the foams fabricated by this procedure is that bioactive agents can be incorporated into foams for sustained release. Fluorescein isothiocyanate (FITC), a fluorescent dye, was used to demonstrate this principle. Distribution of dye in the polymer matrix was evaluated by confocal microscopy, and incorporation of it inside the polymeric foam instead of just surface adsorption is evident. To demonstrate the sustained release of incorporated bioactive agents, bromothymol blue, which has a solubility of 1 mg/ml, was dispersed in the foam and a sustained release over months was obtained (FIG. 1).

Figure 2:
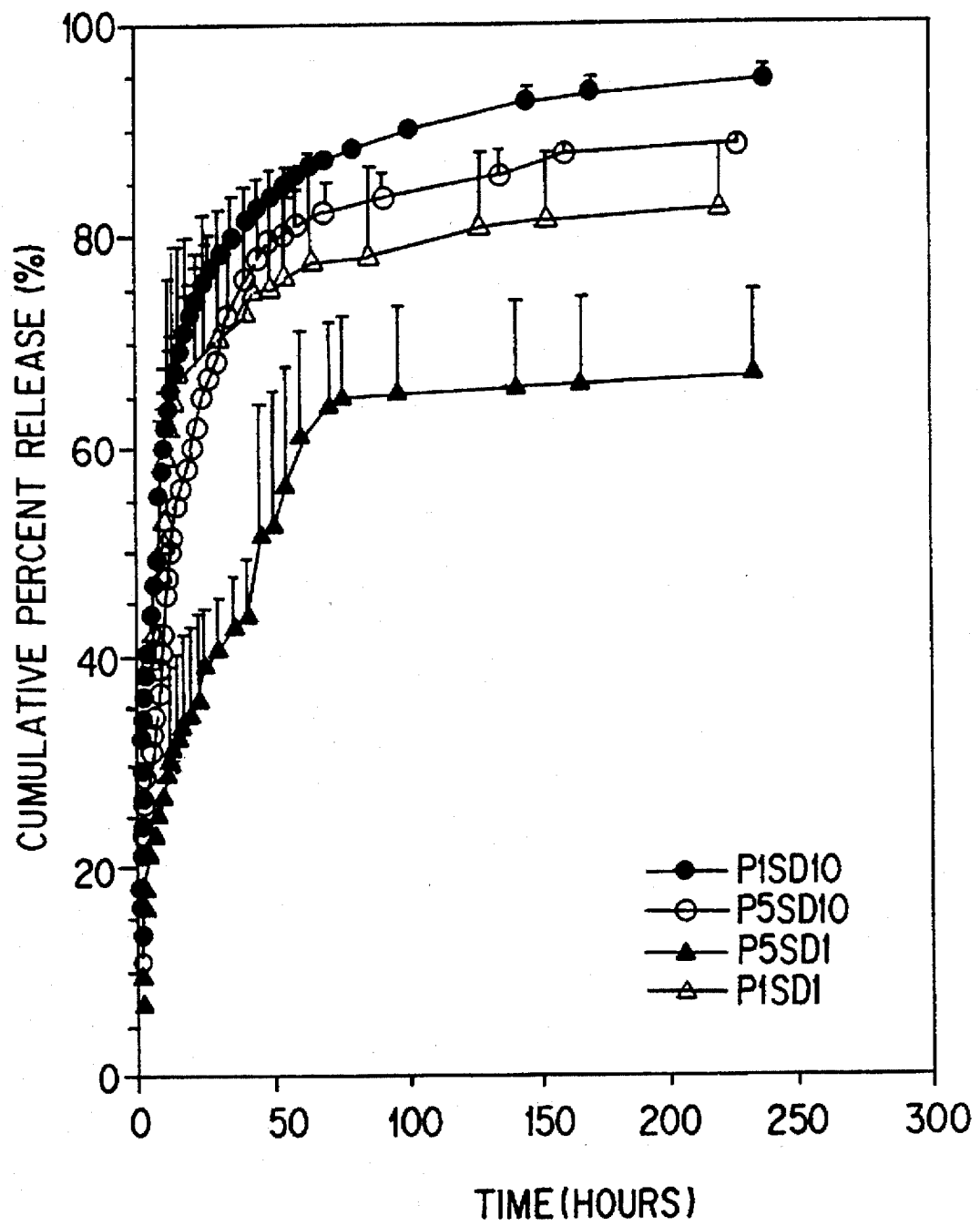
FIG. 2 is a graph showing in vitro release of sulforhodamine B (SD) from PLLA foams in 0.1 phosphate buffer (pH 7.4) at 37° C. Samples of foams made from polymer solutions containing 1 and 5 wt % of PLLA were each loaded with an additional 1 or 10 wt % of SD. P5SD10=10 wt % SD loaded on foam made of 5% PLLA solution.; P5SD1=1 wt % SD loaded on foam made of 5% PLLA solution; P1SD10=10 wt % SD loaded on foam made of 1% PLLA solution; and P1SD1=1 wt % SD loaded on foam made of 1% PLLA solution.

To simulate release of proteins, a hydrophilic dye, sulforhodamine B (SC), which has a solubility of 20 mg/ml was also studied. Due to the high hydrophilicity of SD, there is a high driving force for diffusional release, and most of the dye was released within days (FIG. 2). The most sustained release was obtained for the 5 wt % foam with a 1 wt % loading level. After an initial burst of approximately 60 percent of the embedded dye, there is a much slower but steady release of the remaining dye. The initial burst probably reflects the dye situated at the surface of the macropores of the foam, and the second phase of slow release represents the dye embodied by the polymeric matrix.

EXAMPLE 6

Cell Seeding into Polymer Foams

Rat osteosarcoma (ROS17/2.8) cells were cultured on PLLA and BPA/PP foams after seeding at a density of 10$^4$ cells/ml in 4 ml of medium. The cells were fixed after seventy two hours and stained with propidium iodide for confocal microscopy. A series of images were taken at 50 µm increments into the foam starting at the surface. A representative optical section located 100 µm below the surface of a PLLA foam shows a high number of cells attached to the foam.

Figure 4:
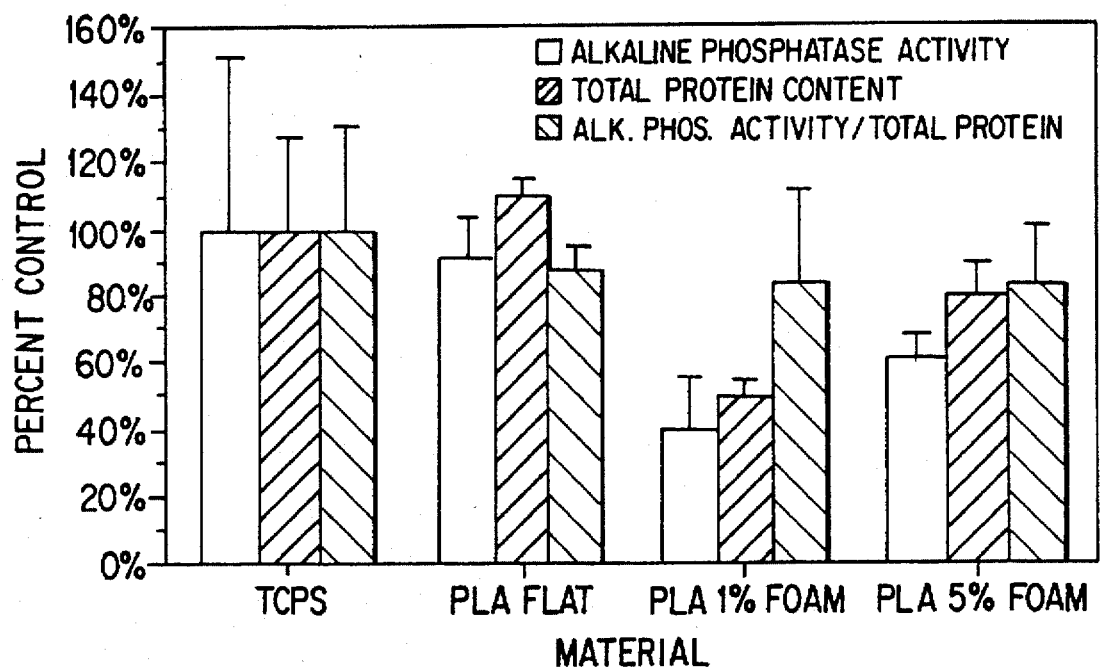
FIG. 4 is a bar graph comparing alkaline phosphatase activity of ROS cells grown on normal tissue culture (TCPS), flat polylactic acid polymer (PLA flat) and polylactic acid foams containing 1 wt % and 0.5% PLA. Solid bars=alkaline phosphatase activity; diagonally crosshatched bars=total protein content; and stippled bars=alkaline phosphatase activity as a fraction of total protein content.

As shown in FIG. 4, the functional activity of the ROS17/2.8 cells was also determined by assaying for alkaline phosphatase and total protein synthesis. The activity of the cells on the PLLA foams was compared to the activity of the cells on flat PLLA surfaces and also on tissue culture polystyrene (TCPS) surface. The specific alkaline phosphatase production of the cells, which is defined as the production of alkaline phosphatase normalized by the total protein synthesis of the cells, was comparable on the foams and flat surfaces. The specific alkaline phosphatase activity is a marker of the functional activity of the ROS cells. The cell seeding number used was high enough to achieve a confluent layer of cells on the flat surfaces, but owing to the much higher surface area of the foams as compared to the flat surfaces, the cell layer was sub confluent on the foams. Keeping in mind that the ROS 17/2.8 cells are a monolayer cell line and express optimal alkaline phosphatase activity at confluency, it was a positive indication that the specific alkaline phosphatase activity on the foams was virtually similar to that on the flat surface, even though the cell layer on the foam was sub confluent.

EXAMPLE 7

Biological Activity Assay

To determine the effect of the fabrication technique upon biological activity of an enzyme, the activity of alkaline phosphatase loaded into the polymer foam scaffold was monitored. As shown in FIG. 3, after residing in the molten napthlene for a total time of 60 minutes, about 25% of the alkaline phosphatase activity was lost.

Stability of alkaline phosphatase in the fabrication process was examined by diethanloamine assay from Sigma (St.

Louis, Mo.) quality control test procedure. The test temperature of this enzymatic assay was modified to 25° C. Alkaline phosphatase (Sigma) was used as controls with 100% activity. Activity of alkaline phosphatase removed from molten naphthalene after various periods of exposure was measured as follows. One milligram of alkaline phosphatase per milliliter of 1000 mM pH 9.8 diethanolamine buffer with 0.5 mM magnesium chloride and 150 mM p-nitrophenyl phosphate (PNPP) solution were incubated separately at 25° C. 2.7 ml of buffer solution and 0.3 ml PNPP solution were then mixed by inversion and allowed to equilibrate to 25° C. Absorbance at 405 nm was monitored using a UV-visible spectrophotomer (Shimadzu model UV-160) until constant readings were obtained. One-tenth ml of enzyme solution was subsequently mixed and the increase in absorbance at 405 nm was recorded for approximately 5 minutes. Slope of absorbance versus time using the maximum linear rate for both the test and blank was obtained. Activity per milligram of enzyme was then calculated by the difference in the slope between the test and blank and divided by 18.5, which is the millimolar extinction coefficient of PNPP at 405 nm.

Ten percent of the activity loss was actually due to the sublimation process. Since this foam fabrication procedure requires an exposure time to molten naphthalene at 85° C. of less than one hour, the suitability of this technique for loading proteins into the foam is demonstrated.

The foregoing description of the invention is exemplary for purposes of illustration and explanation. It should be understood that various modifications can be made without departing from the spirit and scope of the invention. Accordingly, the following claims are intended to be interpreted to embrace all such modifications.

We claim:

1. A method for producing a biocompatible and biodegradable porous foam comprising:
   a) dissolving from about 0.5 to 10 weight percent of a biocompatible polymer in a liquid solvent having a melting point in the range from about 30° to about 90° C. to form a polymer solution;
   b) placing the solvent solution onto a form under conditions promoting spinodal decomposition in the solution;
   c) quenching the polymer solution in the form;
   d) sublimating the solvent in the solution; and
   e) obtaining a biocompatible porous foam comprising a substantially continuous polymer phase and a substantially continuous gas phase with substantially uniform pore size and pore distribution and having an average pore size in the range from about 20 to 500 μm, in diameter.

2. The method of claim 1 wherein the solvent is naphthalene.

3. The method of claim 1 wherein the placing is by spraying the polymer solution onto the form in layers.

4. The method of claim 1 wherein the form is a mold.

5. The method of claim 4 wherein the mold is in the shape of a bone.

6. The method of claim 1 wherein from about 1 to 10 weight percent of a cell growth nutrient is added to the polymer solution in step a).

7. The method of claim 6 wherein the nutrient is selected from the group consisting of enzymes, bone morphogenetic proteins (BMP), epidermal growth factor (EGF), fibroblast growth factor (FGF), platelet-derived growth factor (PDGF), insulin-like growth factor (IGF-I and -II), TGF-β, and dexamethason.

8. The method of claim 1 wherein the polymer comprises polylactic acid.

9. The method of claim 8 wherein the pore surface area is from about 1.2905 to 0.79 m$^2$/g, the pore volume is from about 17.747 to 7.198 cm$^3$/g, and the porosity is from about 87 to 71 percent.

10. The method of claim 9 wherein the polymer solution is quenched while in the early stages of spinodal decomposition.

11. The method of claim 1 wherein the polymer is a polyphosphoester.

12. The method of claim 1 further comprising adding a therapeutic amount of a drug to the polymer solution in step a).

13. The method of claim 12 wherein the polymer solution is quenched while in the early stages of spinodal decomposition.

14. A three dimensional biocompatible and biodegradable porous foam comprising a substantially continuous polymer phase and a substantially continuous gas phase with substantially uniform pore size and pore distribution and having an average pore size in the range from about 20 to 500 μm; and cultured tissue cells contained within the pores.

15. The porous foam of claim 14 wherein the polymer phase comprises polylactic acid.

16. The porous foam of claim 15 wherein the pore surface area is from about 1.2905 to 0.79 m$^2$/g, the pore volume is from about 17.747 to 7.198 cm$^3$/g, and the porosity is from about 87 to 71 percent.

17. The porous foam of claim 15 wherein the polymer phase further comprises a cell nutrient.

18. The porous foam of claim 15 wherein the polymer phase further comprises a therapeutic amount of a drug.

19. The porous foam of claim 14 wherein the density of the cultured tissue cells is about 10$^4$ cells/ml of culture.

20. A biodegradable and biocompatible porous foam comprising a substantially continuous polymer phase and a substantially continuous gas phase with substantially uniform pore size and pore distribution, said foam also including a cell growth nutrient.

21. The porous foam according to claim 20 including cultured tissue cells in the pores.

22. The porous foam according to claim 20 including at least one drug.

23. The method of claim 1 including adding a cell growth nutrient to the polymer solution while forming the polymer solution.

24. The method of claim 1 wherein the polymer comprises a co-polymer.

* * * * *